United States Patent [19]

Junji et al.

[11] Patent Number: 5,534,513

[45] Date of Patent: Jul. 9, 1996

[54] ANTITUMOR POTENTIATOR AND ANTITUMOR COMPOSITION

[75] Inventors: Uchida Junji; Okabe Hiroyuki; Takechi Teiji; Takeda Setsuo, all of Tokushima; Yamada Yuji, Tokorozawa, Japan

[73] Assignee: Taiho Pharmaceutical Company, Ltd., Tokyo, Japan

[21] Appl. No.: 158,476

[22] Filed: Nov. 29, 1993

Related U.S. Application Data

[63] Continuation of Ser. No. 849,413, Apr. 29, 1992, abandoned.

[30] Foreign Application Priority Data

Sep. 5, 1991 [JP] Japan ..................... 2-238719

[51] Int. Cl.$^6$ .................. A61K 31/495; A61K 31/50; A61K 31/505
[52] U.S. Cl. .............................. 514/249; 514/274
[58] Field of Search ..................... 514/274, 249

[56] References Cited

U.S. PATENT DOCUMENTS 4,507,301  3/1985  Fuji et al. ...................... 514/274

OTHER PUBLICATIONS

Chemical Abstracts 107:89123r (1987).
Partial translation of "Biochemical Modulation", vol. 141 No. 9, Date: May 30, 1987.
Complete English translation of "Biochemical Modulation"(Igaku no Ayumi, 1987, 141 (9), 572–275).

*Primary Examiner*—Jerome D. Goldberg
*Attorney, Agent, or Firm*—Nikaido, Marmelstein, Murray & Oram

[57] ABSTRACT

The invention provides;
an antitumor potentiator for potentiating the antitumor activity of an antitumor composition containing tegafur in a therapeutically effective amount and uracil in an amount effective for potentiation of antitumor effect, characterized by containing a folinic acid or a pharmaceutically acceptable salt thereof in an amount effective for potentiation of antitumor effect as an active ingredient;

an antitumor composition characterized by containing tegafur in a therapeutically effective amount, uracil in an amount effective for potentiation of antitumor effect and folinic acid or a pharmaceutically acceptable salt thereof in an amount effective for potentiation of antitumor effect;

a method of potentiating the antitumor effect of an antitumor composition characterized by administering the above antitumor potentiator to a patient; and a method for therapy of cancer in mammalian animals characterized by administering the above antitumor composition to a patient.

9 Claims, No Drawings

ANTITUMOR POTENTIATOR AND ANTITUMOR COMPOSITION

This application is a continuation of U.S. application Ser. No. 07/849,413, filed as PCT/JP91/01187, Sep. 5, 1991 published as WO92/04028 Mar. 19, 1992, now abandoned.

TECHNICAL FIELD

The present invention relates to an antitumor potentiator, an antitumor composition, and the use of them.

BACKGROUND ART

Much research and development work about antitumor agents have been made and clinically various excellent antitumor agents are in use for the chemotherapy of malignant tumors. The outcomes of such therapies have been improved year after year but the efficacies are only transitory in many instances and are not necessarily sufficient to arrest growth of tumors and assure patients of long life spans. By way of illustration, tegafur is a substance which is activated in the living body to release 5-fluorouracil (hereinafter referred to as 5-FU), the substance of its antitumor activity, and was designed to alleviate the toxicity or adverse effect of 5-FU. The advent of a combination drug consisting of tegafur and uracil is predicated on the idea that while 5-FU is rapidly metabolized and loses its activity in the body, this inactivation is inhibited by uracil which has no antitumor activity of its own to thereby achieve a marked potentiation of the antitumor effect.

However, the current status of cancer therapy points to the need for development of drugs having higher antitumor activity.

DISCLOSURE OF THE INVENTION

Under the circumstances the inventors of the present invention were energetically engaged in the research for enhancing the antitumor effect of the tegafur-uracil combination drug and found that the use of folinic acid which has no antitumor activity of its own in combination with a tegafur-uracil combination drug results in a marked potentiation of the antitumor effect of the combination drug without increasing its toxicity (particularly digestive organ toxicity). The present invention has been developed on the basis of the above finding.

Thus, the present invention provides an antitumor potentiator for potentiating the antitumor activity of an antitumor composition containing tegafur in a therapeutically effective amount and uracil in an amount effective for potentiation of antitumor effect, the potentiator being characterized by containing folinic acid or a pharmaceutically acceptable salt thereof in an amount effective for potentiation of antitumor effect as an active ingredient, and an antitumor composition characterized by containing tegafur in a therapeutically effective amount, uracil in an amount effective for potentiation of antitumor effect and folinic acid or a pharmaceutically acceptable salt thereof in an amount effective for potentiation of antitumor effect.

The antitumor potentiator of the present invention is capable of potentiating the antitumor effect of the known tegafur-uracil combination drug without increasing its toxicity (particularly digestive organ toxicity).

Tegafur is a drug which is activated in the body to release 5-FU, the substance of its activity, and is a known compound.

Tegafur is produced by the known production technology, for example by the process described in Japanese Examined Patent Publication No. 10510/1974. On the other hand, uracil has no antitumor activity of its own but inhibits the metabolic inactivation of 5-FU in the body to markedly potentiate its antitumor effect.

Therefore, the present invention provides a method for therapy of cancer in mammalian animals comprising administering to a mammalian animal tegafur in a therapeutically effective amount, uracil in an amount effective for potentiation of antitumor effect and folinic acid or a pharmaceutically acceptable salt thereof in an amount effective for potentiation of antitumor effect and a method for further potentiating the antitumor effect resulting from administration of an antitumor composition for mammalian animals containing tegafur in a therapeutically effective amount and uracil in an amount effective for potentiation of antitumor effect to a patient with cancer responsive to 5-fluorouracil therapy, the method being characterized by administering folinic acid or a pharmaceutically acceptable salt thereof in an amount effective for potentiation of antitumor effect to the same patient.

The proportions of tegafur and uracil in the antitumor combination drug to be used in conjunction with the antitumor potentiator of the present invention may be the same as that used in the known combination drug. Thus, based on each mole of tegafur, the proportion of uracil is generally 0.02 to 10 moles and preferably 0.1 to 10 moles.

Folinic acid which is used in the antitumor potentiator of the present invention has heretofore been used chiefly for the purpose of mitigating the toxicity of folic acid antagonists and no antitumor action has been reported in this compound as such. Folinic acid exists in d- or l- form as optical isomer and any of these isomers as well as mixture thereof can be employed in the present invention. The use of the l-isomer or a mixture of l- and d-isomers is particularly beneficial. The pharmaceutically acceptable salt of folinic acid includes, for example, the corresponding calcium salt.

While the proper proportion of folinic acid or a salt thereof varies according to clinical requirements and is not specifically limited, it is generally 0.05 to 10 moles and preferably 0.1 to 5 moles per mole of tegafur.

The antitumor potentiator of the present invention can be independently processed into various dosage forms and administered either independently of or simultaneously with the tegafur-uracil combination drug which may also have been processed into various dosage forms. Thus, the antitumor potentiator can be administered any time before, after or simultaneously with the administration of the tegafur-uracil combination drug. Preferably, it is administered simultaneously or within 4 hours and more preferably 2 hours before or after administration of the tegafur-uracil combination drug.

In the present invention, an antitumor potentiator-containing antitumor composition can be provided by incorporating folinic acid or a salt thereof in a tegafur-uracil combination drug. This antitumor composition can be processed into various dosage forms and administered. In such cases, the proportions of tegafur, uracil and folinic acid or a salt thereof may be the same as mentioned above, i.e. 0.02 to 10 moles, preferably 0.1 to 10 moles, of uracil and 0.05 to 10 moles, preferably 0.1 to 5 moles, of folinic acid or a salt thereof based on each mole of tegafur.

The present invention provides, as mentioned above, a mixed pharmaceutical composition containing an antitumor potentiator comprising folinic acid or a salt thereof in combination with a tegafur-uracil combination drug or a pharmaceutical composition comprising said antitumor potentiator and said tegafur-uracil combination drug as two independent units. Either of these compositions can be manufactured by the conventional method using a suitable pharmaceutical carrier. The carrier for this purpose may include those widely used for common pharmaceuticals, such as excipients, binders, disintegrators, lubricants, colorants, corrigents, flavors, surfactants and so on.

Furthermore, the above antitumor potentiator and the tegafur-uracil combination drug can be provided in the form of a kit comprising a combination of the following pharmaceutical compositions for therapy of cancer in mammalian animals, namely (a) an antitumor composition containing tegafur in a therapeutically effective amount and uracil in an amount effective for potentiation of antitumor effect, and (b) a composition containing folinic acid or a pharmaceutically acceptable salt thereof in an amount effective for potentiation of the antitumor effect of said antitumor composition.

In this kit, the respective constituent compositions can be provided in optional known dosage forms and generally these compositions are accommodated in appropriate containers selected according to particular dosage forms.

Moreover, this kit may be a kit for therapy of cancer in mammalian animals which comprises at least three components and at least two containers for said components, said three components comprising:

(i) tegafur in a therapeutically effective amount, (ii) uracil in an amount effective for potentiation of antitumor effect, and (iii) folinic acid or a pharmaceutically acceptable salt thereof in an amount effective for potentiation of the antitumor effect of the above antitumor composition, said tegafur and said folinic acid or salt thereof being packaged in different containers.

The respective components of the kit of the invention can be administered simultaneously or one before or after the other at an appropriate interval. Preferably, they are administered concurrently or one within 4 hours, preferably 2 hours, before or after administration of the other. According to the kit of the present invention, the antitumor effect of the antitumor composition containing tegafur and uracil is remarkably enhanced by the composition containing folinic acid or a pharmaceutically acceptable salt thereof without increasing the level of toxicity such as digestive organ toxicity.

There is no limitation on the unit dosage form which can be adopted for the antitumor potentiator or antitumor composition of the invention in the treatment of malignant tumors in mammalian animals inclusive of human beings. Thus, optional unit dosage forms can be selected according to the purpose of treatment. Thus, for example, various non-oral dosage forms such as injections, suppositories, ophthalmic solutions, ointments, aerosols, etc. and various oral dosage forms such as tablets, coated tablets, powders, granules, capsules, solutions, pills, suspensions, emulsions, etc. can be mentioned. These dosage forms can be manufactured by the pharmaceutical procedures well established in this field.

As the carrier for the manufacture of solid dosage forms for oral administration, such as tablets, powders, granules, etc., there can be employed various excipients such as lactose, sucrose, sodium chloride, glucose, urea, starch, calcium carbonate, kaolin, crystalline cellulose, silicic acid, methylcellulose, glycerol, sodium alginate, gum arabic, etc.; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, water, ethanol, potassium phosphate, etc.; disintegrators such as dry starch, sodium alginate, agar powder, laminaran powder, sodium hydrogen carbonate, calcium carbonate, polyoxyethylene-sorbitan fatty acid esters, sodium lauryl sulfate, stearic acid monoglyceride, starch, lactose, etc.; antidisintegrators such as sucrose, stearic acid, cacao butter, hydrogenated oil, etc.; absorption promotors such as quaternary ammonium bases, sodium lauryl sulfate, etc.; humectants such as glycerol, starch, etc.; adsorbents such as starch, lactose, kaolin, bentonite, colloidal silicic acid, etc.; and lubricants such as purified talc, stearic acid salts, boric acid powder, polyethylene glycol and so on. The tablets may be coated, where necessary, to provide sugar-coated tablets, gelatin-coated tablets, enteric-coated tablets, film-coated tablets, double or multi-layer tablets and so on.

The carrier for shaping into the form of pills includes, for example, various excipients such as glucose, lactose, starch, cacao butter, hardened vegetable oil, kaolin, talc, etc.; binders such as gum arabic powder, gum tragacanth powder, gelatin, etc.; and disintegrators such as laminaran, agar and so on.

Capsules are manufactured by mixing the antitumor potentiator, either alone or together with a tegafur-uracil combination drug, with any of the carriers mentioned above and filling the mixture in hard gelatin capsule, soft capsule or other capsules.

The carrier for shaping into the form of suppositories include, for example, polyethylene glycol, cacao butter, lanolin, higher alcohols, esters of higher alcohol, gelatin, semi-synthetic glycerides, Witepsol (Resistered trademark for the product of Dynamit Nobel) and so on.

The carrier for shaping into the form of injections includes, for example, various diluents such as water, ethyl alcohol, macrogols, propylene glycol, ethoxylated isostearyl alcohol, polyoxylated isostearyl alcohol, polyoxyethylene-sorbitan fatty acid esters, etc.; pH control agents and buffers such as sodium citrate, sodium acetate, sodium phosphate, etc.; and stabilizers such as sodium pyrosulfite, EDTA, thioglycollic acid, thiolactic acid and so on. In these injections, it is allowable to incorporate sodium chloride, glucose or glycerol in an amount sufficient to provide an isotonic solution or to add the conventional solubilizer, soothing agent local anesthetic or the like. After addition of these carriers, injections for subcutaneous, intramuscular or intravenous administration can be manufactured by the established procedures.

The liquid dosage form includes aqueous or oily suspensions, solutions, syrups, elixirs, etc. and can be manufactured by the established pharmaceutical procedures using the usual additives.

The diluent for the manufacture of ointments, such as pastes, creams, gels, etc., includes, for example, white petrolatum, paraffin, glycerol, cellulose derivatives, polyethylene glycol, silicon compounds, bentonite and so on.

The amount of folinic acid or a pharmaceutically acceptable salt thereof, which is the active ingredient of the antitumor potentiator of the present invention, or the amounts of tegafur, uracil and folinic acid or a pharmaceutically acceptable salt thereof, which are the active ingredients of the antitumor composition of the invention, are dependent on the dosage form, route of administration, dosing schedule, etc. and can be appropriately chosen. Generally, however, the total amount of active substance or substances in the dosage form may range from about 1 to about 70 percent by weight.

The route of administration of the antitumor potentiator or antitumor composition of the present invention may for example be intestinal, oral, rectal, stomatic, percutaneous or the like and can be freely selected according to the dosage form, the patient's age, sex and other factors, the clinical condition of the patient and so on. By way of example, tablets, pills, solutions, suspensions, emulsions, granules and capsules are orally administered. Suppositories are inserted into the rectum. Ointments are applied to the skin, the intraoral mucosa or the like.

In the present invention, the dosage of each active ingredient in each pharmaceutical composition can be selected according to the method of administration, the patient's age, sex and other factors, the degree of disease and so on. In the case of oral administration, the standard dosage is about 0.1 to 100 mg/kg/day, preferably about 1 to 30 mg/kg/day, for tegafur, about 0.1 to 100 mg/kg/day, preferably 1 to 50 mg/kg/day, for uracil and about 0.1 to 500 mg/kg/day, preferably 0.2 to 300 mg/kg/day, for folinic acid or a pharmaceutically acceptable salt thereof. The compositions of the invention can each be administered daily in a single dose or in 2 to 4 divided doses. In the case of injections, e.g. intravenous injections, the equivalent of, generally, about 1 to 50 mg/kg of tegafur per day per adult is optionally diluted with physiological saline or glucose injection and is administered gradually over a period of not less than 5 minutes. In the case of suppositories, the equivalent of about 1 to 100 mg/kg of tegafur per adult is administered into the rectum once to twice a day at an interval of 6 to 12 hours.

The malignant tumors which can be treated with the compositions of the invention may be any of the tumors responsive to 5-fluorouracil which is the active substance. Among them are cancers of the head and neck, stomach, colon, rectum, liver, gallbladder-bile duct, pancreas, lung, breast, urinary bladder, prostate, uterine cervix and so on. Particularly high success rates can be expected in colon cancer, rectal cancer and mammary cancer.

EXAMPLES

Some formulation examples of the antitumor potentiator of the invention and some formulation examples of the antitumor composition with the antitumor potentiator of the invention are presented below as examples of the invention.

Formulation Example 1

| Folinic acid | 100 mg |
|---|---|
| Lactose | 170 mg |
| Crystalline cellulose | 77 mg |
| Magnesium stearate | 3 mg |
| | 350 mg per capsule |

Using the established pharmaceutical procedure, capsules were prepared according to the above formula.

Formulation Example 2

| Calcium folinate | 200 mg |
|---|---|
| Lactose | 340 mg |
| Corn starch | 450 mg |
| Hydroxypropylmethylcellulose | 10 mg |
| Granules | 1,000 mg |

Using the established pharmaceutical procedure, granules were prepared according to the above formula.

Formulation Example 3

| Folinic acid | 500 mg |
|---|---|
| Lactose | 240 mg |
| Corn starch | 250 mg |
| Hydroxypropylmethylcellulose | 10 mg |
| Fine granule | 1,000 mg |

Using the established pharmaceutical procedure, fine granules were prepared according to the above formula.

Formulation Example 4

| Folinic acid | 50 mg |
|---|---|
| Lactose | 90 mg |
| Crystalline cellulose | 30 mg |
| Magnesium stearate | 2 mg |
| Talc | 3 mg |
| Hydroxypropylmethylcellulose | 10 mg |
| | 185 mg per tablet |

Using the established pharmaceutical procedure, tablets were prepared according to the above formula.

Formulation Example 5

| Calcium folinate | 200 mg |
|---|---|
| Distilled water for injection | q.s. |
| | 5 ml per ampule |

Using the established pharmaceutical procedure, an injection was prepared according to the above formula.

Formulation Example 6

| Tegafur | 50 mg |
|---|---|
| Uracil | 112 mg |
| Folinic acid | 250 mg |
| Lactose | 280 mg |
| Corn starch | 298 mg |
| Hydroxypropylmethylcellulose | 10 mg |
| | 1,000 mg per wrapper |

Using the established pharmaceutical procedure, granules were prepared according to the above formula.

Formulation Example 7

| Tegafur | 50 mg |
|---|---|
| Uracil | 112 mg |
| Calcium folinate | 75 mg |
| Lactose | 103 mg |
| Crystalline cellulose | 57 mg |

| | |
|---|---|
| Magnesium stearate | 3 mg |
| | 400 mg per capsule |

Using the established pharmaceutical procedure, capsules were prepared according to the above formula.

Formulation Example 8

| | |
|---|---|
| Tegafur | 25 mg |
| Uracil | 56 mg |
| Calcium folinate | 25 mg |
| Lactose | 52 mg |
| Crystalline cellulose | 15 mg |
| Magnesium stearate | 3 mg |
| Corn starch | 14 mg |
| Hydroxypropylmethylcellulose | 10 mg |
| | 200 mg per tablet |

Using the established pharmaceutical procedure, tablets were prepared according to the above formula.

Formulation Example 9

| | |
|---|---|
| Tegafur | 200 mg |
| Uracil | 448 mg |
| Folinic acid | 500 mg |
| Witepsol W-35 | 852 mg |
| | 2,000 mg per suppository |

Using the established pharmaceutical procedure, suppositories were prepared according to the above formula.

EXAMPLE 1

A 2 mm-diameter fragment of mouse colon cancer line COLON 26 was subdermally transplanted at the back of male $CDF_1$ mice. Beginning 24 hours after transplantation of the tumor fragment, a solution or suspension of tegafur-uracil combination drug, 5-fluorouracil and calcium folinate, the amounts of which are indicated below in Table 1, in 0.5% sodium calboxymethylcellulose (CMC) solution was administered orally once a day for 9 consecutive days. On day 12 after transplantation of the tumor fragment, the tumor was enucleated and weighed. From the ratio of the mean tumor weight in each treatment group to that in the control group, the tumor growth inhibition rate was calculated. On the other hand, the body weight of mice on the day of tumor fragment transplantation was subtracted from the body weight of mice exclusive of tumors on day 12 after transplantation and the difference was used as the index of drug-induced systemic toxicity. Furthermore, the stools passed by mice in each treatment group were examined daily and, in accordance with the method described in Japanese Journal of Cancer Research Vol. 81, 188–195 (1990), the stool property was rated on the following scale: −: normal stool (hard pellets with little moisture), ±: loose stool (normal form, moist and soft), +: loose stool (undefinable form, very moist and soft), ++: diarrheal stool (formless, watery).

The results are set forth in Table 1.

TABLE 1

| Drug | Dosage (mg/kg) | Folinic acid (mg/kg) | Tumor Growth inhibition rate (%) | Change in body weight (g) | Stool property |
|---|---|---|---|---|---|
| Tegafur + uracil | 20.0 + 44.8 | 0 | 45 | +1.8 | ± |
| Tegafur + uracil | 20.0 + 44.8 | 100 | 79 | +1.5 | ± |
| Tegafur + uracil | 15.0 + 33.6 | 0 | 43 | +1.9 | ± |
| Tegafur + uracil | 15.0 + 33.6 | 100 | 65 | +1.6 | ± |
| 5-Fluorouracil | 20.0 | 0 | 43 | +1.7 | ± |
| 5-Fluorouracil | 20.0 | 100 | 56 | +0.1 | ++ |

EXAMPLE 2

A 2–3 mm-diameter fragment of mouse colon cancer line COLON 38. was subdermally transplanted at the back of 6-week-old male $BDF_1$ mice and the mice in which the tumor volume (major diameter×minor diameter$^2$/2) had reached 100–200$^3$ mm were used in groups each consisting of 7 in the following experiment.

The mice were dosed orally with a solution or suspension of tegafur-uracil combination drug and calcium folinate, the amounts of which are indicated below in Tables 2 and 3, in 0.5% sodium carboxylmethylcellulose (CMC) solution once a day for 9 consecutive days.

The antitumor efficacies were evaluated as follows. Using a pair of calipers, the tumor volume was measured serially and the tumor growth inhibition rate was calculated from the ratio of the mean tumor volume in each treatment group to that in the control group. On the other hand, the body weight of mice on the day of tumor fragment transplantation was subtracted from the body weight of mice exclusive of tumors on day 10 after transplantation and the difference was used as the index of drug-induced systemic toxicity.

The results are set forth in Tables 2 and 3.

TABLE 2

| Drug | Dosage (mg/kg) | Folinic acid (mg/kg) | Tumor Growth inhibition rate (%) | Change in body weight (g) |
| --- | --- | --- | --- | --- |
| Tegafur + uracil | 20.0 + 44.8 | 0 | 76 | +0.3 |
| Tegafur + uracil | 20.0 + 44.8 | 100 | 98 | +0.6 |

TABLE 3

| Drug | Dosage (mg/kg) | Folinic acid (mg/kg) | Tumor Growth inhibition rate (%) |
| --- | --- | --- | --- |
| Tegafur + uracil | 20.0 + 44.8 | 0 | 79 |
| Tegafur + uracil | 20.0 + 44.8 | 6.7 | 94 |
| Tegafur + uracil | 20.0 + 44.8 | 25 | 90 |
| Tegafur + uracil | 20.0 + 44.8 | 67 | 91 |
| Tegafur + uracil | 20.0 + 44.8 | 100 | 94 |
| Tegafur + uracil | 20.0 + 44.8 | 167 | 91 |
| Tegafur + uracil | 20.0 + 44.8 | 250 | 93 |

EXAMPLE 3

A 2–3 mm-diameter fragment of human colon cancer line KM20C was subdermally transplanted at the back of 6-week-old female BALB/c-nu/nu mice and the mice in which the tumor volume (major diameter×minor diameter$^2$/2) had reached 100–200 mm$^3$ were used in groups each consisting of 7 in the following experiment.

The mice were dosed orally with a solution or suspension of tegafur-uracil combination drug and calcium folinate, the amounts of which are indicated below in Table 4, in 0.5% sodium carboxymethylcellulose (CMC) solution once a day for 10 consecutive days.

The antitumor efficacies were evaluated as follows. Using a pair of calipers, the tumor volume was measured serially and the tumor growth inhibition rate was calculated from the ratio of the mean tumor volume in each treatment group to that in the control group. On the other hand, the body weight of mice on the day of tumor fragment transplantation was subtracted from the body weight of mice exclusive of tumors on day 12 after transplantation and the difference was used as the index of drug-induced systemic toxicity.

The results are set forth in Table 4.

TABLE 4

| Drug | Dosage (mg/kg) | Folinic acid (mg/kg) | Tumor Growth inhibition rate (%) | Change in body weight (g) |
| --- | --- | --- | --- | --- |
| Tegafur + uracil | 20.0 + 44.8 | 0 | 3 | −0.3 |
| Tegafur + uracil | 20.0 + 44.8 | 100 | 36 | −0.5 |

We claim:

1. A method for further potentiating the antitumor effect resulting from administration of an antitumor composition to a patient with a cancer wherein the cancer is sensitive to treatment with the combinations shown below, wherein the antitumor composition contains tegafur and uracil in a molar ratio of 1:4, said method comprising administering folinic acid or a pharmaceutically acceptable salt thereof in an amount effective for potentiation of antitumor effect to said patient.

2. The method of claim 1 wherein the effective amount of folinic acid or a pharmaceutically acceptable salt thereof is 0.01– 5.0 moles per mole of tegafur.

3. The method of claim 1 wherein the effective amount of folinic acid or a pharmaceutically acceptable salt thereof is 0.05– 5.0 moles per mole of tegafur.

4. The method of claim 1 wherein folinic acid or a pharmaceutically acceptable salt thereof is administered to the patient within 4 hours either before or after administration of said antitumor composition.

5. The method of claim 1 wherein folinic acid or a pharmaceutically acceptable salt thereof is administered to the patient within 2 hours either before or after administration of said antitumor composition.

6. The method of claim 1 wherein folinic acid or a pharmaceutically acceptable salt thereof is administered to the patient simultaneously with said antitumor composition.

7. The method of claim 1 wherein the compounds are administered by oral administration.

8. An antitumor composition comprising tegafur, uracil and folinic acid or a pharmaceutically acceptable salt thereof, in a molar ratio of 1:4:0.01–5.0.

9. The composition of claim 8 wherein the ratio is 1:4:0.05–5.0.

* * * * *

UNITED STATES PATENT AND TRADEMARK OFFICE
CERTIFICATE OF CORRECTION

PATENT NO. : 5,534,513
DATED : July 9, 1996
INVENTOR(S) : Uchida et al.

It is certified that error appears in the above-indentified patent and that said Letters Patent is hereby corrected as shown below:

On the title page,

Item [75], line 1, delete "Uchida Junji" insert therefor -- Junji Uchida --. Also, delete "Okabe Hiroyuki" insert therefor -- Hiroyuki Okabe --. Item [75], line 2, delete "Takechi Teiji" insert therefor -- Teiji Takechi --. Also, delete "Takeda Setsuo" insert therefor -- Setsuo Takeda --. Item [75], line 3, delete "Yamada Yuji" insert therefor -- Yuji Yamada --. Item [30], line 1, delete "September 5, 1991" insert therefor --September 7, 1990--.

UNITED STATES PATENT AND TRADEMARK OFFICE
CERTIFICATE OF CORRECTION

PATENT NO. : 5,534,513
DATED : July 9, 1996
INVENTOR(S) : Uchida et al.

It is certified that error appears in the above-indentified patent and that said Letters Patent is hereby corrected as shown below:

On the title page, insert item --[63] Continuation of Ser. No. 849,413, filed Apr. 29, 1992, abandoned, which was the national stage of international application number PCT/JP91/01187, filed Sept. 5, 1991--.

Signed and Sealed this

Seventh Day of January, 1997

Attest:

BRUCE LEHMAN

*Attesting Officer*  *Commissioner of Patents and Trademarks*